United States Patent [19]

Park et al.

[11] Patent Number: 4,836,196

[45] Date of Patent: Jun. 6, 1989

[54] SURGICALLY IMPLANTABLE SPINAL CORRECTION SYSTEM

[75] Inventors: Joon B. Park; James N. Weinstein; Vijay K. Goel, all of Iowa City, Iowa

[73] Assignee: AcroMed Corporation, Cleveland, Ohio

[21] Appl. No.: 142,493

[22] Filed: Jan. 11, 1988

[51] Int. Cl.⁴ ............................................. A61F 5/04
[52] U.S. Cl. ........................... 128/92 YM; 128/92 YJ
[58] Field of Search ............ 128/69, 92 YL, 92 YM, 128/92 YJ, 92 YF, 92 YE; 403/408.1, 90, 122; 411/542, 544, 537, 907, 908, 943, 963, 149, 150, 155, 156, 159

[56] References Cited

U.S. PATENT DOCUMENTS

| | | | |
|---|---|---|---|
| 2,219,423 | 10/1940 | Kurtz | 411/537 X |
| 3,648,691 | 3/1972 | Lumb et al. | 128/92 YM |
| 3,659,595 | 5/1972 | Haboush | 128/92 YL |
| 4,322,193 | 3/1982 | Stahl | 411/11 |
| 4,594,026 | 6/1986 | Hauer et al. | 403/408.1 X |
| 4,611,581 | 9/1986 | Steffee | 128/69 |
| 4,653,481 | 3/1987 | Howland et al. | 128/69 |

FOREIGN PATENT DOCUMENTS

| | | | |
|---|---|---|---|
| 1079393 | 4/1960 | Fed. Rep. of Germany | 411/537 |
| 1066581 | 1/1984 | U.S.S.R. | 128/69 |
| 780652 | 8/1957 | United Kingdom | 128/69 |

OTHER PUBLICATIONS

DuPont Bulletin, 4/1954, pp. 1-3, "The Properties of DuPont Nylon Resin".

Primary Examiner—Robert A. Hafer
Assistant Examiner—Kevin G. Rooney
Attorney, Agent, or Firm—Tarolli, Sundheim & Covell

[57] ABSTRACT

An apparatus for connecting a structure with a vertebral body of a spinal column and for transmitting a load between the structure and the vertebral body. The apparatus includes a fastener with a threaded portion for threaded engagement with a surface defining an opening in the vertebral body to connect the vertebral body with the structure. A spacer is adapted to be located between the fastener and the structure for transmitting load therebetween. The spacer is made of a material which plastically deforms as a function of time and load applied thereto to decrease the load transmitted between the vertebral body and the structure.

11 Claims, 5 Drawing Sheets

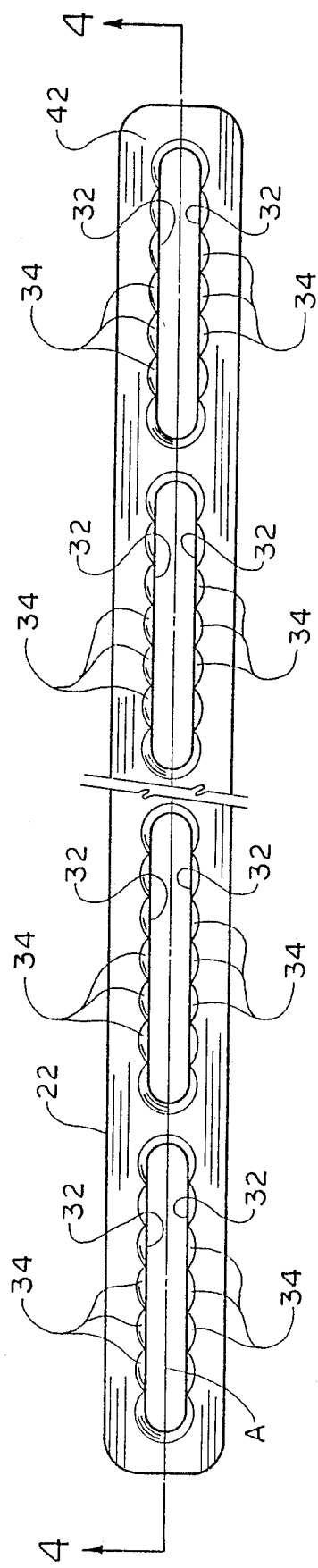
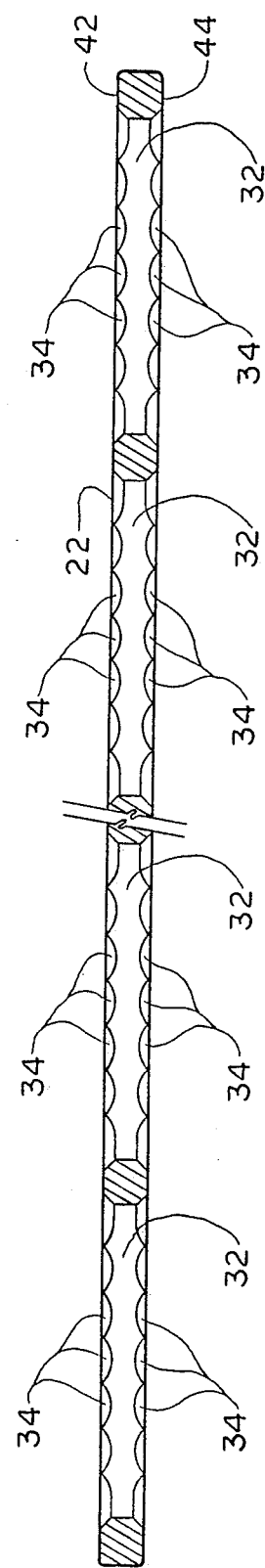
FIG. 3
FIG. 4

SURGICALLY IMPLANTABLE SPINAL CORRECTION SYSTEM

BACKGROUND OF THE INVENTION

1. Technical Field

The present invention relates to the correction of spinal columns. In particular, the present invention relates to a surgically implantable device for maintaining vertebral bodies of the spinal column in a desired relationship during healing of a portion of the spinal column.

2. Description of the Prior Art

It is known that spinal columns, particularly human spinal columns, are prone to deformation and degeneration. These conditions often require surgery to correct. During one type of surgical procedure, at least one of the intervertebral discs is removed from a damaged portion of the spinal column. Bone graft is prepared and is placed in the position from which the damaged disc has been removed. A device is connected with the vertebral bodies on opposite sides of the bone graft to maintain the vertebral bodies in a desired relationship and to prevent load from being transmitted through the bone graft. It is desirable to prevent the transmission of load through the bone graft immediately after surgery because the bone graft is not in a healed condition sufficient enough to transmit load therethrough.

U.S. Pat. No. 4,611,581 discloses such a device for connection with vertebral bodies. The device includes an elongate plate having a plurality of openings arranged along the longitudinal central axis of the plate. Fasteners are received in the openings to connect the plate with the vertebral bodies. The plate is relatively rigid and transmits load of the spinal column through the plate so the load is not transmitted through the bone graft.

However, the implantable device generally transmits load of the spinal column therethrough long after the bone graft has healed. In some instances, it is felt, that because the surgically implantable device transmits a relatively large portion of the load therethrough that the bone graft does not heal as quickly as if some load was transmitted through the bone graft. It is believed that bone graft heals more quickly if, as it heals, the load transmitted through the bone graft progressively increases.

A known external fixation device, such as disclosed in U.S. Pat. No. 1,789,060, is used on other bones in the body to reduce bone fractures and promote their healing. The known external fixation device has a portion extending outside of the body. The device can be adjusted to decrease the portion of the load transmitted through the device and concurrently increase the portion of the load transmitted through the healing bone. It has been found that such a procedure promotes better healing of the injured bone.

However, it is impractical to have a portion of the aforementioned surgically implanatable device connected to vertebral bodies of a spinal column extending outside of the body for adjustment during the course of healing of the bone graft. It is also impractical to perform surgery each time an adjustment is desired on the implanted device. Thus, it will be apparent that a need exists for a completely internal apparatus connectable with vertebral bodies of a spinal column and which decreases the amount of load transmitted therethrough as bone graft heals and thereby increases the load transmitted through the vertebral bodies and bone graft for promoting healing of the bone graft.

SUMMARY OF THE INVENTION

The present invention relates to a surgically implantable apparatus connectable with vertebral bodies of the spinal column. The apparatus is completely contained within the human body and provides for gradually decreasing the load transmitted between the apparatus and the vertebral bodies to promote the healing of the bone graft located between the vertebral bodies. Such an apparatus provides significant advantages over heretofore known devices which either cannot be adjusted without surgery subsequent to their implantation or which have a portion for adjustment external to the body.

The apparatus for the correction of a portion of the spinal column, according to the present invention, includes a structure for connecting together a pair of vertebral bodies of the spinal column. Bone graft is disposed between the pair of vertebral bodies. Fasteners connect the structure with the pair of vertebral bodies. A load is transmitted between the pair of vertebral bodies through the structure. The percentage of the load transmitted through the structure decreases as a function of time as the bone graft heals to thereby increase the percentage of the load transmitted through the bone graft.

A spacer is located between the structure and one of the fasteners for transmitting load therebetween. The spacer decreases the load transmitted between the structure and fastener as a function of time. The spacer is made of a material which plastically deforms as a function of time and load transmitted therethrough to decrease the load transmitted between the structure and the fastener.

The material the spacer is made from is an ultra-high-molecular-weight polyethylene. The spacer has an opening therethrough for receiving a portion of one of the fasteners. The spacer also has an exterior surface for receipt in a matching recess in the structure to block sliding movement of the plate relative to the fastener.

BRIEF DESCRIPTION OF THE DRAWINGS

Further features of the present invention will become apparent to those skilled in the art to which the present invention relates from reading the following specification with reference to the accompanying drawings, in which:

FIG. 3 is a plan view of a plate which is part of the apparatus of FIG. 1;

FIG. 4 is a cross sectional view of the plate of FIG. 3 taken approximately along line 4—4 of FIG. 3;

DESCRIPTION OF A PREFERRED EMBODIMENT

Figure 1:
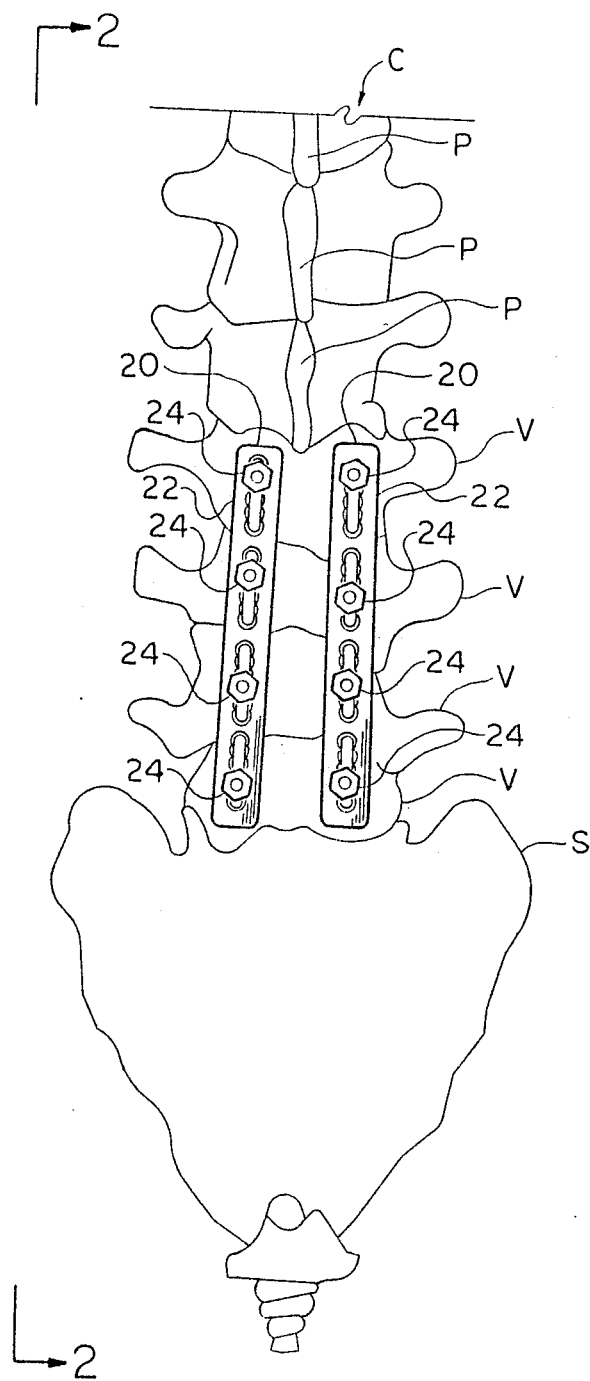
FIG. 1 is a view of a surgically implantable apparatus, embodying the present invention, connected with vertebral bodies of a spinal column.

The apparatus, illustrated in FIG. 1, according to the present invention, includes a pair of surgically implantable devices 20 connected with vertebral bodies V of a spinal column C. It will be apparent that the surgically implantable devices 20 may be placed anywhere along the spinal column C and connected with any of the vertebral bodies V or sacrum S, as deemed necessary by a surgeon. Bone graft G (FIG. 2) is prepared in a known manner and is placed between some of the vertebral bodies V to replace discs D which have been damaged or injured. Each of the surgically implantable devices 20 maintain the vertebral bodies V in a desired predetermined relationship and prevent load being transmitted through the bone graft immediately after the operation.

The surgically implantable devices 20 transmit loads applied to the spinal column C therethrough to promote the healing of the bone graft G after surgery. The surgically implantable devices 20 transmit a relatively large portion of the load of the spinal column C therethrough immediately after the surgical procedure. This is necessary to prevent any large loads being transmitted to the newly formed bone graft G. The load may be any combination of tensile, compressive, torsional load or any other load acting on the spinal column C.

Figure 2:
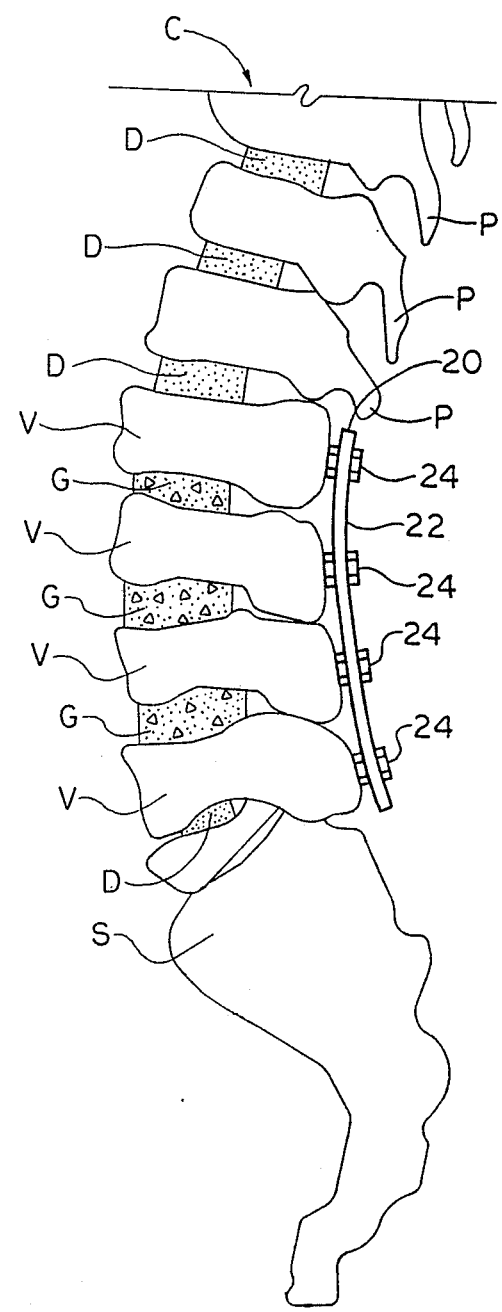
FIG. 2 is a side view of the apparatus in FIG. 1 taken approximately along the line 2—2 of FIG. 1.

FIGS. 1 and 2 illustrate that the spinous processes P have been removed from the vertebral bodies V which are spanned by the devices 20. The spinous processes P are illustrated here as having been removed for clarity and may not be necessary during the operation, as is known.

Each of the surgically implantable devices 20 includes a structure or plate 22 connected with the vertebral bodies V by a plurality of fasteners 24. While a specific structure, namely, the plate 22 (FIGS. 3 and 4) is illustrated, it will be apparent that other structures, such as rods and clamps, or other configurations of the plate may be used to connect the vertebral bodies V and to transmit load.

The plate 22 is of sufficient length to span four adjacent vertebral bodies V. It will be apparent that a plate 22 having a different length may be used, depending on the exact requirements of the patient. The plate 22 is elongate and is relatively rigid. The plate 22 is bendable to conform to a desired curvature of the portion of the spinal column C spanned, as illustrated in FIG. 2.

The plate 22 (FIGS. 3 and 4) has a plurality of elongate openings 32 extending in a direction parallel to the longitudinal central axis A of the plate. The openings 32 permit the plate 22 to be moved along the fasteners 24 to provide some adjustability in locating the plate along the spinal column C. The number and configuration of the openings 32 in the plate 22 is dependent upon the size of the plate, the number of vertebral bodies V to be connected and other needs of the patient. For example, in a preferred embodiment, four vertebral bodies V are connected with the plate 22, thus, four openings 32 and four fasteners 24 are used.

Each of the openings 32 extends through the plate 22. Each of the openings 32 as a plurality of recesses 34 spaced along the length of the opening. Each of the recesses 34 is for receiving a portion of a spacer 72 therein, as is described below. Each of the recesses 34 preferably has a surface defined by a portion of a sphere. The recesses 34 are located in both of the opposite major side surfaces 42, 44 (FIG. 4) of the plate 22. Each of the recesses 34 receive a portion of the spacer 72 to block the relative sliding movement between the plate 22 and a fastener 24 connected to one of the vertebral bodies V.

Figure 5:
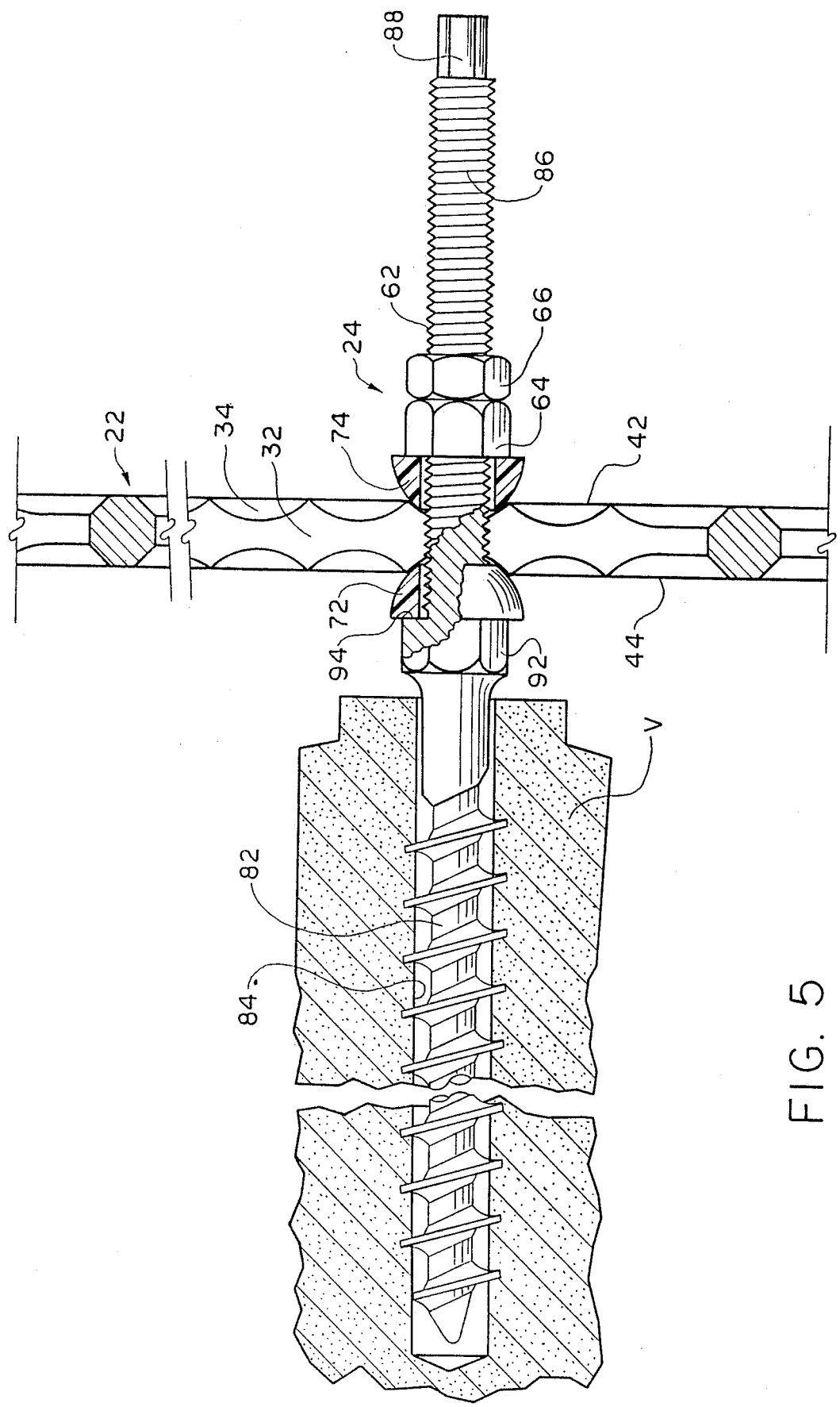
FIG. 5 is an enlarged cross sectional view of a portion of the apparatus connected with a vertebral body.
Figure 6:
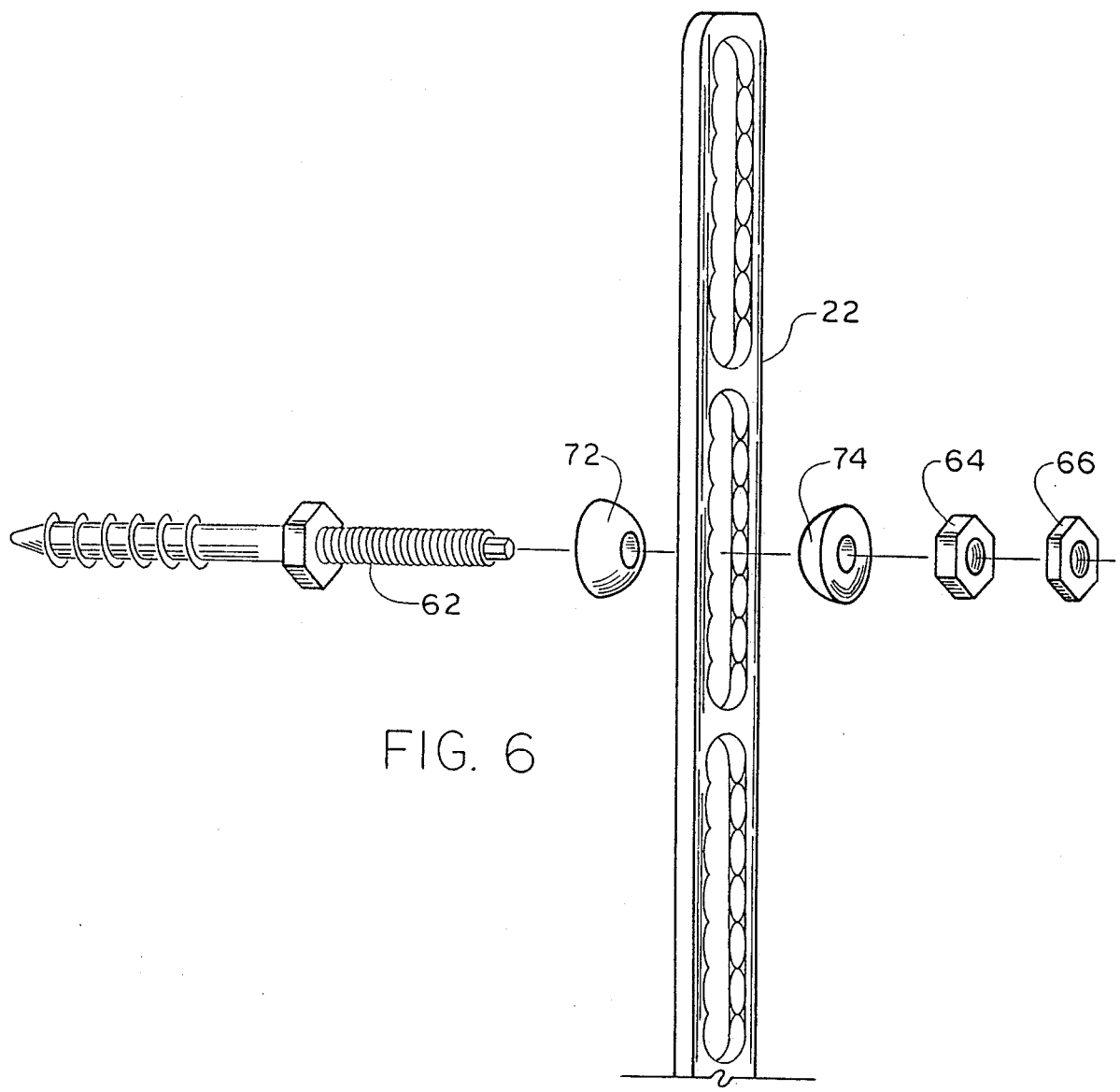
FIG. 6 is an exploded perspective view of a portion of the apparatus embodying the present invention.

Each of the fasteners 24 (FIGS. 5 and 6) includes a screw 62 and a pair of nuts 64, 66. Each of the fasteners 24 connect the plate 22 with a respective one of the vertebral bodies V. It will be apparent that other types of fasteners 24 may be used to connect the plate 22 with the vertebral bodies V of the spinal column C.

The screw 62 (FIG. 5) has a first threaded portion 82 for threaded engagement with a surface defining an opening 84 in the vertebral body V. The screw 62 also has a second threaded portion 86 for threaded engagement with the nuts 64, 66. A hex head end portion 88 of the screw 62 is used to thread the screw 62 into the opening 84 in the vertebra during the surgical procedure. The screw 62 also has an intermediate portion 92 which has a hexagonal configuration to be gripped by a suitable tool (not shown). The intermediate portion 92 of the screw 62 includes a planar surface defining a shoulder 94 for engaging the spacer 72. The intermediate portion 92 establishes the distance that the spacer 72 and, thus, the plate 22 are located away from the vertebral body V.

After the screw 62 is threaded into the opening 84 in the vertebral body V, the spacer 72 is placed over the second threaded end portion 86 so that a planar surface 76 (FIG. 8) of the spacer rests against the shoulder 94 of the intermediate portion 92. The plate 22 is then placed over the screw 62 so that one of the recesses 34 in the major side surface 44 closely fits an exterior surface 78 of the spacer 72 having a shape of a portion of a sphere. A second spacer 74, identical to the spacer 72, is received on the second threaded end portion 86 of the screw 62. An exterior surface of the spacer 74 having a shape of a portion of a sphere is brought into engagement with a recess 34 in the major side surface 42 of the plate 22 and opposite the spacer 72.

The nut 64 is then threaded onto the second threaded portion 86 and is tightened against the spacer 74 while a suitable tool grips the intermediate portion 92 to prevent rotation of the screw 62. The nut 64 is tightened sufficiently to exert a clamping force on the spacers 72, 74 to maintain the position of the plate 22 relative to the screw 62 of the fastener 24, and thereby relative to the vertebral body V. Thus, load is transferred between the vertebral body V to the fastener 24 through the spacers 72, 74 and to the plate 22, or vice versa. The second nut 66 is threaded onto the second threaded portion 86 and engages the nut 64 to serve as a jam nut to prevent a loosening of the nut 64 and a loosening of the clamping force. The portion of the second threaded portion 86 of the screw 62 extending beyond the second nut 66 may then be trimmed away in a known manner.

Figure 7:
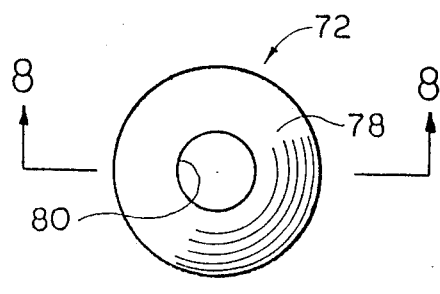
FIG. 7 is an enlarged plan view of a spacer of the apparatus.
Figure 8:
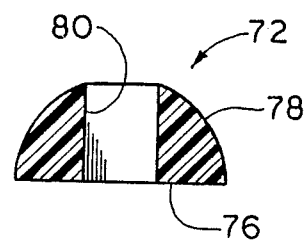
FIG. 8 is a cross sectional view of the spacer in FIG. 7 taken approximately along line 8—8 of FIG. 7.
Figure 9:
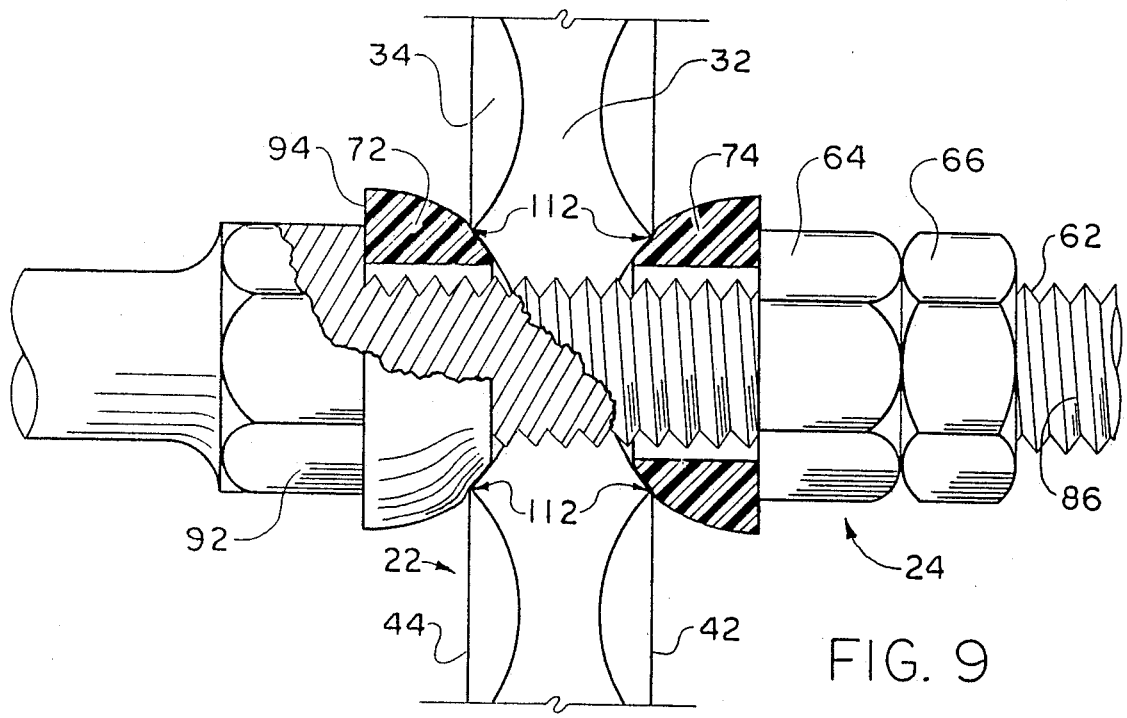
FIGS. 9 and 10 are enlarged views of a portion of FIG. 5 illustrating different exaggerated conditions of the spacers.

The spacers 72, 74 are identical (only one of which is illustrated in FIGS. 7 and 8) in shape, size and material. The spacer 72 is made of a material which is somewhat elastic and which creeps or plastically deforms as a function of time and load transmitted through the spacer. The plastic deformation of the material of the spacer 72 tends to reduce the load transmitted between the fastener 24 and the plate 22. The material that the spacer 72 is made from is preferably an ultra-high-molecular-weight polyethylene. It is known that polyethylene is subject to creep and stress relaxation under loading. The spacer 72 has an opening 80 extending therethrough for receiving a portion of the screw 62. The planar surface 76 of the spacer 72 extends in a direction perpendicular to the opening 80. It will be apparent that a spacer 72 made from other materials or having a different configuration may be used. For example, the spacers 72 may be adhesively bonded to the recesses in the plate 22 for ease of handling during the surgical procedure.

Figure 10:
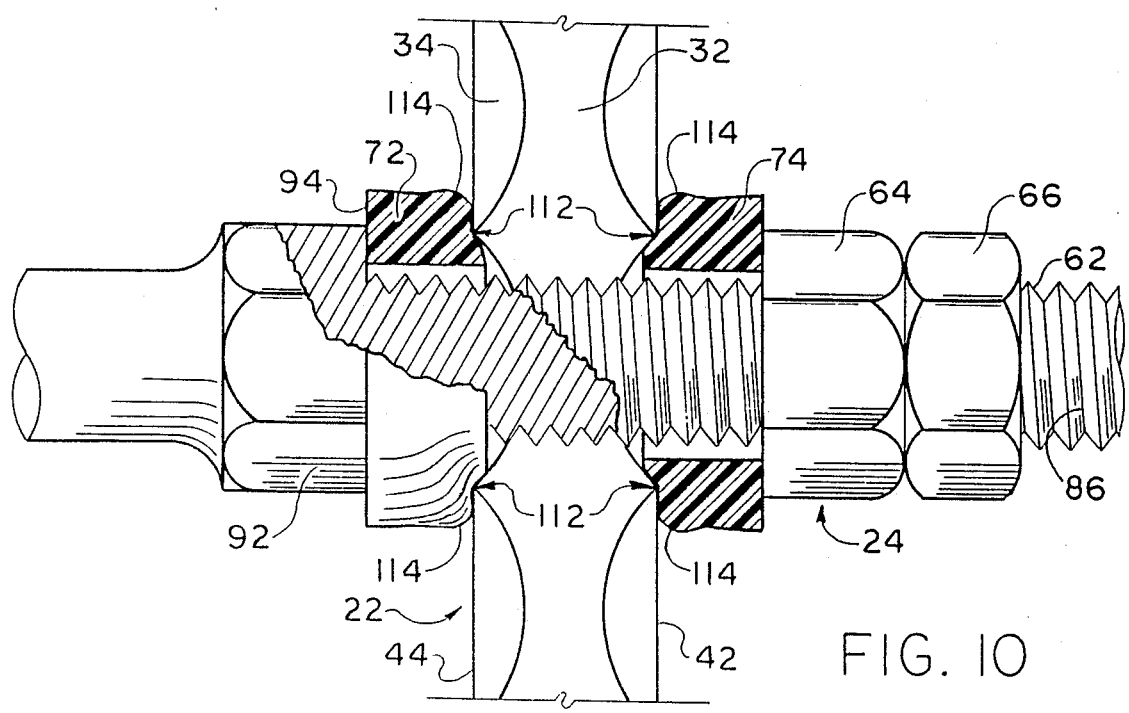

When the spacers 72, 74 are initially clamped to the plate 22, they are compressed slightly so that portions 112 of each spacer are depressed inwardly. This compression of the spacers 72, 74 assures that a relatively large portion of the load of the spinal column C is transmitted between the fastener 24 and the plate 22 through the spacers. Over time, the material of the spacers 72, 74 creeps or plastically deforms under the load transmitted between the plate 22 and the fasteners 24. This creep or plastic deformation is illustrated in FIG. 10 as a portion 114 (shown exaggerated) of the spacers 72, 74 which over time flows and decreases compression of the material. Thus, the load transmitted between the fastener 24 and plate 22 decreases because the spacers 72, 74 lose compression over time. Concurrently, the load of the spinal column C transmitted through the vertebral bodies V and bone graft G increases. Thus, more load is applied through the bone graft G as it heals to promote healing thereof. The load is also more naturally transmitted through the vertebral bodies V adjacent the vertebral bodies connected with the plate 22. This gradual loading of the bone graft G and vertebral bodies V connected by the plate 22 as the bone graft heals promotes better healing.

The thickness of the portion of the spacers 72, 74 disposed between the screw 62 and plate 22 determines the amount of plastic deformation and the time for the deformation to effect a decrease in the load transmitted from the fastener 24 to the plate 22. For example, relatively thick spacers 72, 74 will take a longer time to plastically deform to a degree in which minimum load is transmitted between the fastener 24 and the plate 22 than relatively thin spacers. A time duration of approximately six months after the surgical procedure is believed to be optimal for decreasing the load transmitted between the fastener 24 and plate 22 from a relatively large percentage of the load of the spinal column C to a relatively small percentage. At this time, the bone graft G would be substantially healed.

From the above description of a preferred embodiment of the invention, those skilled in the art will perceive improvements, changes and modifications. Such improvements, changes and modifications within the skill of the art are intended to be covered by the appended claims.

Having described a specific preferred embodiment of the present invention, we claim the following:

1. A surgically implantable apparatus for connecting together a pair of vertebral bodies of the spinal column wherein bone graft is located between the pair of vertebral bodies, said apparatus comprising:
a structure for transmitting load between the pair of vertebral bodies so the bone graft is substantially free from load immediately after surgery;
fastener means for connecting said structure with each one of the pair of vertebral bodies; and
means for increasing the load transmitted through the bone graft as the bone graft heals, said means being locatable between said structure and said fastener means for transmitting load therebetween and for increasing the load transmitted through the bone graft by decreasing the load transmitted between said structure and said fastening means as a function of time.

2. The apparatus set forth in claim 1 wherein said means for increasing the load includes a spacer made of a material which plastically deforms as a function of time to decrease the load transmitted between said fastener means and said structure.

3. The apparatus set forth in claim 2 wherein said material is an ultra-high-molecular-weight polyethelene.

4. The apparatus set forth in claim 2 wherein said spacer includes an exterior surface having the shape of a portion of a sphere and wherein said structure further includes surface means defining a recess with the shape of a portion of a sphere for receiving said spacer, said spacer further including surface means defining an opening for receiving a portion of said fastener means therethrough.

5. The apparatus set forth in claim 1 wherein said structure comprises a plate including surface means defining an opening extending through said plate for receiving a portion of said fastener means.

6. The apparatus set forth in claim 1 wherein said fastener means includes a screw having a first threaded portion for threaded engagement with one of the vertebral bodies, a second threaded portion, and a shoulder portion located intermediate said first and second threaded portions for spacing said structure from the vertebral body, said fastener means further includes a nut for threaded engagement with said second threaded portion of said screw on a side of said structure opposite said shoulder portion of said screw to apply a clamping force to said structure and to said means for increasing the load upon tightening of said nut.

7. An apparatus for use with a surgically implantable structure, which structure interconnects a pair of vertebral bodies in a spinal column, wherein bone graft is located between the pair of vertebral bodies, and wherein the structure transmits load between the pair of vertebral bodies so that bone graft is substantially free form load immediately after surgery, said apparatus comprising:
a fastener for connecting one of the vertebral bodies with the structure and having a threaded portion for threaded engagement with the one vertebral body; and
a first member locatable between said fastener and the structure for transmitting load between said fastener and the structure and for increasing the load transmitted through the bone graft as the bone graft heals by decreasing the load transmitted between said fastener and the structure;
said first member being made of a material which plastically deforms as a function of time and load transmitted therethrough to decrease the load transmitted between said fastener and the structure.

8. The apparatus set forth in claim 7 wherein said first member includes an exterior surface having the shape of a portion of a sphere and surface means defining an opening for receiving a portion of said fastener therethrough.

9. The apparatus set forth in claim 7 wherein said material is an ultra-high-molecular-weight polyethelene.

10. The apparatus set forth in claim 7 wherein said fastener includes a screw having a first threaded portion for threaded engagement with a vertebral body, a second threaded portion, and a shoulder portion located intermediate said first and second threaded portions for spacing the structure from the vertebral body, said fastener further including a nut for threaded engagement with said second threaded portion of said screw on a side of the structure opposite said shoulder portion of said screw to apply a clamping force to the structure and said first member upon tightening of said nut.

11. The apparatus set forth in claim 7 further including a second member locatable between said fastener and the structure on a side of the structure opposite said first member, said second member being made of a material which plastically deforms as a function of time and load transmitted therethrough to decrease the load transmitted between said fastener and the structure.

* * * * *

UNITED STATES PATENT AND TRADEMARK OFFICE
CERTIFICATE OF CORRECTION

PATENT NO.  : 4,836,196

DATED       : June 6, 1989

INVENTOR(S) : Joon B. Park, James N. Weinstein, Vijay K. Goel

It is certified that error appears in the above-identified patent and that said Letters Patent is hereby corrected as shown below:

Column 6, Line 44, change "that" to --the--

Column 6, Line 45, change "form" to --from--

Signed and Sealed this

Sixth Day of March, 1990

*Attest:*

JEFFREY M. SAMUELS

*Attesting Officer*      Acting Commissioner of Patents and Trademarks